United States Patent [19]

Mitzner

[11] 4,128,507

[45] Dec. 5, 1978

[54] PERFUMED GELS OF HYDROXYPROPYL CELLULOSE

[75] Inventor: Bernard M. Mitzner, New Hampton, N.Y.

[73] Assignee: Polak's Frutal Works, Inc., Middletown, N.Y.

[21] Appl. No.: 773,098

[22] Filed: Feb. 28, 1977

[51] Int. Cl.$^2$ ................................................ C11B 9/00
[52] U.S. Cl. ..................................... 252/522; 424/76; 252/316
[58] Field of Search ........................... 252/522; 424/76

[56] References Cited

U.S. PATENT DOCUMENTS 3,609,102  9/1971  Schlossman .......................... 252/522

Primary Examiner—Veronica O'Keefe
Attorney, Agent, or Firm—William S. Alexander

[57] ABSTRACT

Gels are prepared utilizing hydroxypropyl cellulose as the solid matrix phase and a mixture of a linear polyol, a perfume oil and optionally a hydroxypropyl cellulose solvent as the liquid phase.

4 Claims, No Drawings

PERFUMED GELS OF HYDROXYPROPYL CELLULOSE

This invention relates to gel compositions suitable for use as solid air fresheners. More particularly, it relates to a solid air freshener composition utilizing a gel of hydroxypropyl cellulose as the matrix.

During recent years, a number of solid air freshener compositions have been marketed with a reasonable degree of success. These compositions, which are primarily based on carrageenan, release perfume or freshening agent continuously over a period of time. Although carrageenan adequately forms gels and is capable of entrapping perfumes for slow release, the physical properties of the carrageenan gel create a number of problems which must be closely watched during production and formulation. One of the most important problems regarding carrageenan is a problem known as syneresis, i.e., the separation of moisture from the gel which gives the gel surface a wet appearance and can create difficulties. The syneresis problem can be alleviated in carrageenan gels by using sufficiently high percentages of gelling agent. However, carrageenan is an expensive material and it is very difficult to produce an economic solid air freshener gel without having significant amounts of syneresis.

Attempts have been made to alleviate this syneresis problem by incorporating various additional metal ions, such as potassium ions, into the composition. Also, attempts have been made to increase the stability of these materials and decrease syneresis by adding other thickeners, such as guar gum and gelatin, to the system. An example of compositions of the above type are U.S. Pat. No. 2,927,055 and British Pat. No. 1,241,914. However, compositions within the scope of the above patents tend to produce some degree of syneresis depending upon the amount of carrageenan utilized and, accordingly, a satisfactory gel is difficult and expensive to produce.

In addition to the syneresis problem, the prior art carrageenan systems are heat-sensitive gels and, accordingly, production requires both heating and cooling means for proper mixing and processing. These heating and cooling means add significantly to the costs of these prior art systems and further require careful monitoring of the process. Moreover, this heat sensitivity carries over into the finished product, making such gel unsatisfactory in environments where the temperature may occasionally become excessively high as, e.g., in a parked automobile. In areas of high humidity, such as, e.g., basements of houses, perfumes are not released readily due to the lack of evaporation of the water of the gel, thus not making such products efficacious.

Gels from carrageenan also appear to be deficient in the amount of perfume oil that can be incorporated therein and, accordingly, have relatively short useful life. Generally, a carrageenan based product contains no more than a maximum of about 10% perfume oil by weight.

It has been found that stable, heat and syneresis resistant shaped bodies suitable for use as air fresheners can be prepared using, as a matrix, a hydroxypropyl cellulose gel. More specifically, the invention is a solid, self-supporting perfumed gel suitable for use as an air freshener comprising about 3 to 10% by weight of a solid phase consisting essentially of hydroxypropyl cellulose and about 90 to 97% by weight of a liquid phase consisting essentially of about 35 to 90% by weight of a linear polyol plasticizer, about 10 to 55% of a perfume oil, about 0 to 10% of a solvent for hydroxypropyl cellulose selected from the class consisting of water and 1 to 3 aliphatic alcohols.

Hydroxypropyl cellulose is a water-soluble, organo-soluble, thermoplastic cellulose derivative commercially available under the trade name "Klucel" from Hercules Incorporated. It is prepared by reacting alkali cellulose with propylene oxide in an inert solvent whereby the hydroxypropyl moiety attaches to the cellulose molecule through one of the hydroxyl groups present thereon, forming an ether. Three sites for potential substitution are available on each cellulose molecule and, additionally, the hydroxypropyl group, once attached, offers another site for reaction so that, theoretically, any number of hydroxypropyl molecules can be affixed to a single anhydroglucose unit. Normally, however, commercially available hydroxypropyl cellulose will have a substitution level between about 2 and 10 hydroxypropyl molecules per anhydroglucose unit and preferably about 3 to 4. (The substitution level is referred to as the M.S. or molecular substitution.) It is available in low, medium, and high viscosity grades, indicating low, medium, and high molecular weight cellulose. Any of these viscosity grades can be used in the products of this invention. For further information concerning preparation and properties of hydroxypropyl cellulose, reference is made to U.S. Pat. No. 3,278,521.

The linear polyols which can be employed in the perfumed gel of this invention are exemplified by, but not limited to, propylene glycol, trimethylene glycol, trimethylol propane, glycerine, sorbitol, and lanolin. These materials are weak solvents for hydroxypropyl cellulose and are frequently employed as plasticizers for hydroxypropyl cellulose in other applications, although in lower amounts relative to the amount of hydroxypropyl cellulose.

With about 3 to 10% hydroxypropyl cellulose in the matrix, the matrix is actually a very concentrated solution of hydroxypropyl cellulose. Such a solution is so viscous as to be a solid at temperatures up to at least about 160° F. Although the perfumed gels according to this invention are solid and self-supporting, they are actually solutions of hydroxypropyl cellulose in the linear polyol, perfume oil, solvent mixture. Even at quite low concentrations, i.e., 1 to 2%, hydroxypropyl cellulose solutions are extremely viscous in any solvent. In the gel of this invention the viscosity is so great that the solution solidifies. However, in many cases, particularly with lower molecular weight or low concentration of hydroxypropyl cellulose, the gel may be of relatively soft consistency. In this case, the gel can be hardened by the addition of a small amount of a hydroxypropyl cellulose solvent such as water, methanol, ethanol, isopropanol or n-propanol. The reason for this has not been determined, but it is found that by varying the amount of such solvent, gels can be prepared of substantially any desired consistency. Generally, the amount of such solvent is between 0 and 10% and preferably no more than about 5%.

The gel can be of any desired shape. For most air freshener applications, a stick or rod shape is very suitable. In some cases, it is desirable to form decorative shapes. In another embodiment which is very useful for air freshener applications, the gel is placed in a porous, nonwoven plastic bag. The porous nature of the bag allows the perfume to escape quite readily into the surrounding environment. Such a form is ideal as a sachet.

The perfume oil included in the gels of this invention can be any of the conventional commercially available perfume oils. These are complex mixtures of volatile compounds including esters, ethers, aldehydes, alcohols, unsaturated hydrocarbons and terpenes such as are well known to those skilled in the fragrance art. Specific perfume oils are musks, rose oil, honeysuckle oil, pine oil, jasmin and oak moss, for example. Their use as to type and proportion is limited only by their compatibility with hydroxypropyl cellulose and their solubility in the other liquid ingredients.

The significance of varying the rigidity of the matrix as discussed above lies in the rate at which the liquid phase including the perfume can evaporate to the surrounding environment. From a soft matrix, the liquid can evaporate more rapidly than from a more solid matrix. Thus, the specific form of the matrix to be employed will depend upon the environment in which it is intended to be used.

Perfumed gels according to this invention have a variety of uses. The primary utility is as room or space fresheners, e.g., to emanate a fragrance or odor effect such as to mask unpleasant odors in the surrounding environment as, for example, in a bathroom, kitchen or laundry. Specific odorants are available to accomplish this objective and will be known to the practitioner. They can also contain perfume essences such that they can provide a pleasant odor simply for its own sake without regard to an unpleasant odor already present in the environment, for example, they can be used as sachets in closets and chests or to create a specific seasonal atmosphere in a room.

As suggested above, the perfumed gels of this invention are especially suited for use as air fresheners or to provide a pleasant odor in an automobile. Their improved heat resistance as compared to prior art materials developed for this application prevents them from being destroyed by the extremely high temperatures which can sometimes be experienced within a closed automobile in hot summer weather. Shaped bodies can be prepared according to this invention which will withstand temperatures of 150° to 160° F. and retain their integrity.

Gel matrices are easily prepared by simply mixing the ingredients and kneading the mixture until the hydroxypropyl cellulose particles are evenly distributed throughout the liquid (plasticizer-perfume oil-solvent) phase and are partially swollen by the liquid. While the mixture is still fluid, it is placed in a mold and allowed to stand at room temperature until the hydroxypropyl cellulose is thoroughly solvated and the mass is sufficiently rigid to be self-supporting. Normally, about 20 minutes to 1 hour is required for complete solvation, depending upon the temperature and the relative proportions of the ingredients. If necessary, the mixture can be heated to increase the solvation rate.

No ingredients other than those specified above are normally required. However, in some cases it is desirable to add small amounts of other additives such as, e.g., decorative dyes or pigments or preservatives. When used, such materials should be in small amounts, preferably less than 1 or 2% of the entire mass.

The invention is illustrated in the following examples. Parts and percentages are by weight unless otherwise indicated.

EXAMPLE 1

Ten parts of hydroxypropyl cellulose (Klucel G ®) from Hercules Incorporated) was dispersed in a mixture of 40 parts propylene glycol and 50 parts jasmin perfume oil. This mixture was mixed at 25° C. until the hydroxypropyl cellulose was completely softened and swollen, at which point the mass was a very high viscosity fluid. This was placed in a cylindrical mold for about one hour to harden.

When removed from the mold, the hardened body was found to possess the odor of the perfume unchanged from the original. The odor was given off by the body for a period of at least 8 months.

EXAMPLE 2

The procedure of Example 1 was repeated using 5 parts of high molecular weight hydroxypropyl cellulose in 95 parts of a fluid. The fluid mixture contained 45 parts of rose oil, 40 parts propylene glycol and 10 parts methanol.

The mixture was agitated well at 25° C. until a high viscosity fluid was obtained. At this point, the mass was poured into a 3 × 4 inch nonwoven polymer bag lined with perforated polypropylene film and the bag was heat sealed. The perfume odor, substantially unchanged from the original, was given off over a period of at least 6 months.

What I claim and desire to protect by letters patent is:

1. A perfumed gel suitable for use as a room freshener consisting essentially of about 3 to 10% by weight of hydroxypropyl cellulose dissolved in about 90 to 97% of a solution consisting essentially of about 35 to 90% of a linear polyol plasticizer for hydroxypropyl cellulose, 10 to 55% perfume oil and 0 to 10% of a hydroxypropyl cellulose solvent selected from the class consisting of water and 1 to 3 carbon aliphatic ahcohols.

2. A gel according to claim 1 wherein the linear polyol is propylene glycol.

3. A gel according to claim 1 where the solvent is methanol.

4. A gel according to claim 2 where the solvent is methanol.

* * * * *